United States Patent

Harris

Patent Number: 5,689,831
Date of Patent: Nov. 25, 1997

[54] DISPOSABLE EAR COVER

[76] Inventor: Yvette L. Harris, 8820 W. Spokane, Milwaukee, Wis. 53224

[21] Appl. No.: 630,262

[22] Filed: Apr. 10, 1996

[51] Int. Cl.$^6$ .................................................. A61F 11/14
[52] U.S. Cl. .................................................. 2/209; 2/455
[58] Field of Search .................... 2/209, 455; 128/857, 128/864, 866

[56] References Cited

U.S. PATENT DOCUMENTS

| | | |
|---|---|---|
| 2,570,675 | 10/1951 | Heflin . |
| 4,308,623 | 1/1982 | Voorhees . |
| 4,616,643 | 10/1986 | Jung . |
| 4,660,229 | 4/1987 | Harris ................................. 2/209 |
| 4,713,843 | 12/1987 | Duncan . |
| 4,872,219 | 10/1989 | Duncan . |
| 4,916,758 | 4/1990 | Jordan-Ross . |
| 5,243,709 | 9/1993 | Sheehan et al. ......................... 2/455 |

*Primary Examiner*—Diana Biefeld
*Attorney, Agent, or Firm*—Ryan, Maki, Mann & Hohenfeldt

[57] ABSTRACT

An ear protector is formed from a sheet of thin flexible material such as a thermoplastic, for example polyethylene or a coated paper material. The protector is provided with a narrow flap of the sheet material along rear edge, and its top, both of which are curved to approximate the curvature of a human ear. A pressure-sensitive adhesive is provided preferably along the rear edge of the protector to hold the protector in place on the skin behind and adjacent to the ear during use. Preferably the front edge also is provided with a strip of adhesive. The protector has the advantage of being inexpensive and disposable.

8 Claims, 1 Drawing Sheet

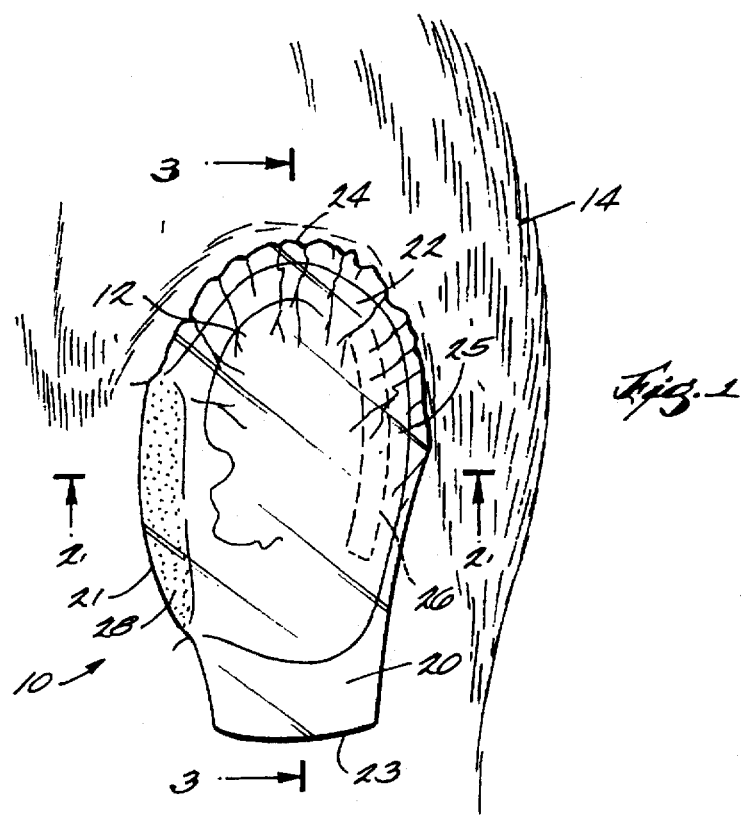
Fig. 1
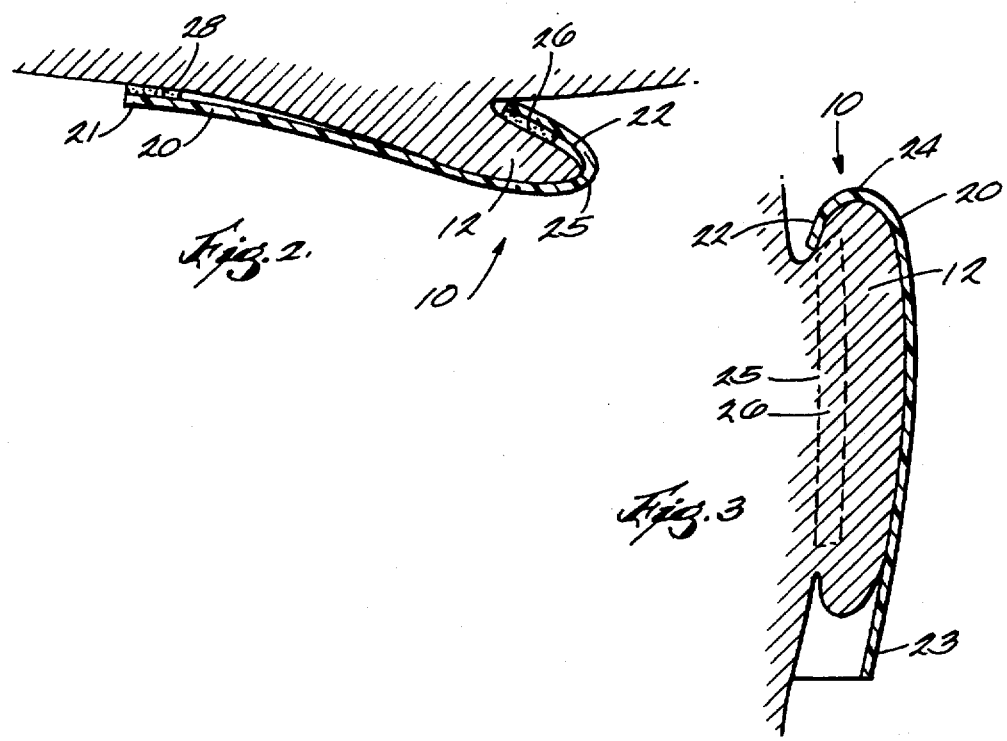
Fig. 2
Fig. 3

DISPOSABLE EAR COVER

This invention relates to an ear protector. More particularly, the invention relates to inexpensive, disposable ear protective devices which are provided with a flap engaging the top and rear of the ear and which include an adhesive for attachment of the protector over the ear.

BACKGROUND OF THE INVENTION

Various ear protective devices have heretofore been provided. Many of such devices proposed in the past have been excessively costly for a single-use basis and thus not disposable. See, for example, U.S. Pat. Nos. 2,570,675, 4,308, 623, 4,616,643, 4,660,229, 4,713,843, 4,872,219 and 4,916, 758.

Even in view of these proposed devices, economical and cost efficient ear protectors are not generally available, and a need has continued to exist for such protectors which are inexpensive enough to be used and disposed of on a single-use basis but which are sufficiently protective to be effective for use by beauticians or by persons suffering from medical ear problems, for example, during showering.

This need has continued to exist particularly for disposable protectors which could be used to protect the ears of the client of a beautician from various hair-treating fluids, such as relaxer creams and like which may burn the ear if allowed to enter therein. Particularly, such need has existed for protectors which are inexpensive enough so that they can be discarded after a single use. A similar need has been experienced relative to a disposable protector for the ears of patients with various medical ear problems for use during showering.

SUMMARY OF THE INVENTION

It is a principal object of the present invention to provide an inexpensive yet effective and convenient single-use ear cover. Ear protectors provided by the invention readily stay fixed in place until removed and are useful in protecting against burns from chemicals such as perms, relaxer cremes or burns from hot irons. Similarly the ears of patients with ear problems can be protected during showering, bathing, or medical procedures.

In accordance with an important aspect of the invention, the cover is held in place over the ear by means of pressure sensitive adhesive placed so that the cover is attached to the skin beneath the ear and adjacent to the scalp, as well as at a point located forwardly of the ear.

In accordance with an important aspect of the invention, such ear covers are formable from inexpensive disposable materials such as thin layers of thermoplastic polymeric materials or alternatively paper coated with a protective plastic layer.

In accordance with a further important aspect of the invention, the cover may be generally flat but with a flap that fits over and approximately conforms to the shape of the top and rear of the ear.

In accordance with yet another aspect of the invention, the ear protector of this invention is provided with a layer of pressure-sensitive adhesive material on the rear and forward edges of the ear protector and, preferably on the interior of the forward edge and the exterior of a rear flap of the ear protector so that attachment is made to the skin beneath the ear, adjacent to the scalp.

Further objects and advantages of the invention will be apparent from the following detailed description and claims, and from the accompanying drawings.

BRIEF DESCRIPTION OF THE DRAWINGS

FIG. 1 is a perspective view of an ear protector of this invention showing it in place on the ear of a fragmentally illustrated user;

FIG. 2 is a sectional view taken along line 2—2 of FIG. 1; and,

FIG. 3 is a sectional view of the protector of FIG. 1 taken along line 3—3.

DETAILED DESCRIPTION OF PREFERRED EMBODIMENT

Referring more specifically to the drawings, an ear protector of this invention is indicated generally by numeral 10. As seen in FIG. 1, ear protector 10 is shaped and adapted to fit over the ear 12 of a user 14.

Protector 10 is formed from a sheet of protective material 20. Sheet 20 may be formed from a polymeric plastic material such as a polyolefin, polyethylene (or a polyvinyl chloride in the event that greater stiffness is preferred.) The sheet 20 which forms protector 10 is provided with a generally flat forward edge 21. The top edge 24 and rear edge 25 of sheet 20 are formed into a curved flap 22 which is shaped to generally fit over and conform to the shape of an ear 12. Top 24 of protector 10 may optionally be gathered or puckered, for example, by embedding therein an elastic cord or the like. It will be apparent to those skilled in the art that protectors 10 of several sizes can be provided for fitting on individual ears of differing sizes.

The bottom edge 23 of sheet 20 is also preferably a free-standing edge cut to a desired length, which should be somewhat longer than enough to extend beyond the bottom of an ear of average length, thereby ensuring the ability to use a cover 10 of a particular selected size on a great number of ears of varying sizes and shapes.

A coating of pressure-sensitive adhesive 26 is preferably provided in the area of flap 22 fitting behind ear 12 as illustrated. Pressure-sensitive adhesive 26 is located in a position to engage the skin beneath the ear, as seen in FIG. 2, and thus assures retention of protector 10 ear 12 but yet allows easy removal thereof when the use of protector 10 has been completed. Another layer 28 of such adhesive serves to hold the front edge of protector 10 in place during use.

A protective release liner can be applied over adhesive coatings 26 and 28 in order to facilitate handling of the protector prior to use thereof and to avoid sticking of various parts of protector 10 to each other.

In applying the protector 10 of the invention, pressure-sensitive adhesive coating 26 first may be exposed by removing its release liner and then applying the same to the user's skin beneath the ear, adjacent to the scalp. Subsequently adhesive 28 adjacent to front edge 21 is attached to the facial skin in front of the ear in order to secure the front of protector 10 in place.

While a protector for a left ear is shown in the drawings, it will be appreciated that protectors 10 would normally be provided in pairs, one to cover the left ear as shown and the other, being a mirror image of the illustrated protector, would be provided for the right ear.

In addition to the use of polymeric plastic materials, sheet 20 can be formed out of other inexpensive materials such as paper which is preferably coated on at least one side with a fluid repellent coating. It will thus be appreciated that the protectors of this invention are readily disposable and sufficiently economical to construct and distribute so that they can be provided as a single-use item.

It will thus be apparent that the protectors herein disclosed can be made widely available for use by beauticians and medical professionals as well as for in home use. Thus the spread of organisms from one client or patient to another, which is always a possibility with reusable items, is avoided It will be apparent to those skilled in the art that various further modifications of the invention can be made without departing from the true scope including equivalents of details set forth in the appended claims. Thus, the foregoing description should be understood to be illustrative rather than restrictive of the details of the invention.

What is claimed:

1. A disposable ear protector comprising a sheet of thin flexible material having top, bottom, front, and rear edges, said front and bottom edges being generally flat and adapted to engage skin in front of and below a wearer's ear, respectively, said top and rear edges being generally adapted to engage the curvature of a human ear, a narrow flap of said flexible sheet material being located along said rear edge, and adapted to fit behind a wearer's ear, a pressure-sensitive adhesive coating on said flap adapted to be affixed to skin beneath a user's ear, whereby said protector can be held in place during use.

2. A protector according to claim 1 wherein said flexible material comprises a thermoplastic polymeric material.

3. A protector according to claim 2 wherein said polymeric material comprises a polyolefin.

4. A protector according to claim 3 wherein said polyolefin comprises polyethylene.

5. A protector according to claim 1 wherein said flexible material comprises paper having a protective plastic coating thereon.

6. A protector according to claim 1 wherein a portion but not all of said flap is coated with said pressure sensitive adhesive.

7. A protector according to claim 1 wherein the top portion of said protector is formed of gathered material.

8. A disposable ear protector comprising a sheet of thin flexible material having top, bottom, front, and rear edges, said top and rear edges being generally adapted to engage the curvature of a human ear, a narrow flap of said flexible sheet material being located along said rear edge, a pressure-sensitive adhesive coating on said flap adapted to be affixed to skin beneath a user's ear, whereby said protector can be held in place during use, and wherein pressure-sensitive adhesive is also coated along a forward edge of said sheet.

* * * * *